United States Patent [19]

Nehra

[11] Patent Number: 5,284,885

[45] Date of Patent: Feb. 8, 1994

[54] AQUEOUS NITROCELLULOSE COMPOSITIONS

[75] Inventor: Samuel A. Nehra, Grosse Pointe Shores, Mich.

[73] Assignee: Agri-Film, Inc., Grosse Pointe Shores, Mich.

[21] Appl. No.: 954,723

[22] Filed: Sep. 29, 1992

[51] Int. Cl.$^5$ .................. C08L 1/00; A61K 7/04
[52] U.S. Cl. ........................ 524/31; 424/61; 536/32; 536/58; 106/195
[58] Field of Search .......... 424/61; 536/32, 58; 106/169, 170, 195; 524/31

[56] References Cited

U.S. PATENT DOCUMENTS

| | | | |
|---|---|---|---|
| 2,099,501 | 11/1937 | Speicher | 106/170 |
| 2,195,971 | 4/1940 | Peter | 167/85 |
| 3,749,769 | 7/1973 | Sugiyama et al. | 424/61 |
| 3,927,203 | 12/1975 | Seymour et al. | 424/61 |
| 4,126,675 | 11/1978 | Boulogne et al. | 424/61 |
| 4,158,053 | 6/1979 | Greene et al. | 424/61 |
| 4,166,110 | 8/1979 | Isobe et al. | 424/61 |
| 4,384,058 | 5/1983 | Galante | 524/32 |
| 4,421,881 | 12/1983 | Benkendorf et al. | 524/24 |
| 4,495,172 | 1/1985 | Orlowski et al. | 424/61 |
| 4,517,324 | 5/1985 | Lühmann et al. | 106/195 |
| 4,649,045 | 3/1987 | Gaske et al. | 424/61 |
| 4,798,720 | 1/1989 | Holder | 424/61 |
| 4,814,015 | 3/1989 | Quinlan | 106/195 |
| 4,820,509 | 4/1989 | Yamazaki et al. | 424/61 |
| 4,822,423 | 4/1989 | Soyama et al. | 106/5 |
| 4,897,261 | 1/1990 | Yamazaki et al. | 424/61 |
| 5,102,654 | 4/1992 | Castrogiovanni et al. | 424/61 |

FOREIGN PATENT DOCUMENTS 0094041 8/1978 Japan .

OTHER PUBLICATIONS

Hercules Incorporated, CSL-132C "Nitrocellulose Lacquer Emulsions-Preparation and Performance for Improving Paper and Paper Products".
Hercules Incorporated, CSL-142A "Nitrocellulose Improved Water Resistance of Polyvinyl Acetate Coatings".
Hercules Incorporated, CSL-225A "Preparation Procedures For Nitrocellulose Waterborne Coatings and Inks".
Kintish, L., Soap Cosmetics Chemical Specialties, Jul. pp. 29-31, 52-53, 58-59 (1992).

*Primary Examiner*—Paul R. Michl
*Assistant Examiner*—LaVonda DeWitt
*Attorney, Agent, or Firm*—Harness, Dickey & Pierce

[57] ABSTRACT

The present invention comprises aqueous nitrocellulose compositions and methods of their making. The compositions of the invention provide coatings and can be employed as nail coatings, protective coatings and non-wax polishes.

8 Claims, No Drawings

AQUEOUS NITROCELLULOSE COMPOSITIONS

FIELD OF THE INVENTION

The present invention relates generally to aqueous nitrocellulose compositions and, more particularly, to aqueous nitrocellulose-based coatings and methods of making.

BACKGROUND OF THE INVENTION

Nitrocellulose has long been used as a base film forming material for various films and coatings. One of its many applications is in lacquer emulsions used in the manufacture of nail coatings or polishes.

Nitrocellulose emulsions used in coatings are generally obtained through either direct emulsification or indirectly through various inversion techniques. For example, a conventional lacquer of nitrocellulose and solvent with emulsifiers is emulsified with the addition of water, inverting from a water-in-lacquer to a lacquer-in-water emulsion. Another inversion technique begins with water-wet nitrocellulose which is dissolved in the solvent system, with water from the mixture dispersing throughout the solvent phase. Additional water containing an emulsifying agent is added forming a lacquer-in-water emulsion by inversion.

Although many improvements have been made in nail coating performance, conventional nail coatings still employ a relatively high percentage of volatile water-immiscible solvents which are relatively toxic, in order to emulsify the nitrocellulose based material. Water-miscible solvents are not ordinarily used because they promote formation of water-in-lacquer rather than lacquer-in-water emulsions. Due to the high percentage of water-immiscible solvents ordinarily employed to emulsify the nitrocellulose, the resultant coatings are flammable and potentially toxic, with a high rate of volatilization and an unpleasant odor. In addition, some individuals become sensitized and develop reactions to these nail coatings.

It is therefore desirable to provide a method for emulsifying nitrocellulose with less reliance on a high percentage of harsh solvents. It is also desirable to provide nitrocellulose-based compositions which have reduced environmental impact by employing a greater percentage of water. It is further desirable to provide nitrocellulose-based compositions for coatings with a lower percentage of solvent. It is further desirable to provide improved nail coatings with a lower percentage of solvents, but which do not sacrifice durability and hardness characteristics.

SUMMARY OF THE INVENTION

The present invention provides novel aqueous nitrocellulose compositions and methods of making such compositions. The present invention also encompasses the use of aqueous nitrocellulose compositions in coatings and the method of making. The coating compositions are free-flowing liquids which may be either pigmented or non-pigmented and applied to human nails in a conventional manner. The coating compositions may also be employed as polishes and protective coatings.

The method for preparing nitrocellulose in water, hereinafter "aqueous nitrocellulose" generally comprises the steps of mixing solid nitrocellulose and a substantial amount of water, adding more water with continued mixing and adding a small amount of solvent with continued mixing. The water and solvent may also be added simultaneously. The above steps are performed at an elevated temperature of about 95° C. to boiling. The resulting mixture is azeotropic-like.

Nitrocellulose-based coatings of the present invention are obtained by mixing a proportional amount of acrylic-based polymers and aqueous nitrocellulose. Various additives such as wetting agents, germicides and thickeners may also be added. Pigmented coatings are formed by adding dispersed treated pigments to the nitrocellulose-based coatings. The dispersed treated pigments are obtained by repeatedly mixing the pigments with silanes, and titanates, desiccating and then, milling the treated pigments with a wetting agent and a dispersing surfactant.

The nail coatings of the present invention are primarily aqueous rather than solvent-based and employ generally gentler, low volatile organic solvents. The hardness, durability and water resistance of the nail coatings of the invention are equal to or surpass those of nail coatings presently on the market. The coatings of the present invention are also less affected by humidity than solvent-based coatings. In addition, the coatings of the present invention have a high solid content (28%-39% solids), which affords better coverage of imperfections in the nail. The coatings of the present invention do not appear to form a continuous film as do solvent-based coatings and do not easily chip due to their adhesive and flexible qualities. The decrease in the high percentage of solvents reduces solvent-related problems. The coatings of the present invention also more readily permit the exchange of body fluids with the atmosphere, i.e. allowing the nail bed to "breathe."

The coatings of the present invention may also be used as a polish on vinyl, leather, finished and unfinished wood, formica and flooring, including linoleum, ceramic tile, marble and mineral flooring and the like. The coatings are also useful as polishes for automobiles.

DETAILED DESCRIPTION OF THE PREFERRED EMBODIMENTS

I. Preparation of Aqueous Nitrocellulose

The nitrocellulose solution is made with solvents selectively compatible with other emulsion vehicles and polymers to which it will be added, to enhance the properties of that particular polymer. Examples of solvents that may be employed in the present invention include but are not limited to propylene glycol monopropyl ether, ethylene glycol monopropyl ether, ethyl 3-ethoxypropionate, isopropyl or ethyl alcohol (32 g) with ethylene glycol monobutyl ether (26 g), dipropylene glycol monobutyl ether, dipropylene glycol methyl ether, propylene glycol methyl acetate, propylene glycol methyl ether acetate, dipropylene glycol methyl ether acetate, isopropyl acetate, N-methyl-2-pyrrolidone, isopropyl or ethyl alcohol and propylene glycol methyl ether. Examples of preferred solvents include propylene glycol monobutyl ether, ethylene glycol monobutyl acetate, ethylene glycol monobutyl ether and diethylene glycol monoethyl ether. The solvents of the present invention may also act as a freeze thaw factor. The present invention may also employ surfactants including but not limited to EI 620, FC129 Fluorad, Surfonyl S-104E, L-7001, and A-196. The invention can also include other additives such as ammonium hydroxide, 28%. The pH of the solution is in the range from about 2.0 to about 6.0.

Nitrocellulose was put into an aqueous solution according to the following general technique wherein the amount of distilled water varied from about 2 parts by weight to about 10 parts by weight for every part by weight of nitrocellulose (all measurements are based on employing an open vessel in the preparation of the compositions). The nitrocellulose was 80% by weight, water packed. An example of preferred nitrocellulose is that sold by Aqualon, a Hercules Corporation. The solvents employed range from about 2 parts by weight to about 10 parts by weight for every part by weight of nitrocellulose. The surfactants employed vary from about 0.05 g to about 0.3 g without dilution for every part by weight of nitrocellulose. The general technique consists of applying heat in the range of from about 70° C. to about boiling, preferably at about 95° C. to about boiling and mixing at a mixer speed of around 8.5 or at a speed great enough to form a vortex in the mixture. Nitrocellulose and distilled water are mixed for about five minutes. More water is added and the solution is mixed for about five more minutes. Solvent is added and mixed for about twenty more minutes. Variations of this method may be employed as illustrated by the foregoing examples with similar results obtained.

The following are examples of the most preferred methods of preparing aqueous nitrocellulose:

Specific Example 1

10 g of nitrocellulose and 20 g of distilled water were mixed for 5 minutes. 20 g of distilled water was added and the resulting solution mixed for 5 minutes. 40 g of ethylene glycol monobutyl acetate was poured into this solution and mixed for 20 minutes.

Specific Example 2

10 g of nitrocellulose and 20 g of distilled water were mixed for 5 minutes. 20 g of distilled water was added and the resulting solution mixed for 5 minutes. 40 g of ethylene glycol monobutyl ether was poured into the mixture and mixed for 20 minutes.

Specific Example 3

10 g of nitrocellulose and 20 g of distilled water were mixed for 5 minutes. 20 g of distilled water was added and the resulting solution mixed for 5 minutes. 0.5 g of CMC-7H-1% was added and this solution was mixed for 8 minutes. 40 g of ethylene glycol monobutyl ether was then poured into the solution and mixed for 20 minutes.

Specific Example 4

10 g of nitrocellulose and 20 g of distilled water were mixed for 5 minutes. 20 g of distilled water was poured into the mixture and mixed for 5 minutes. 0.5 g of CMC-7H-1% was added and mixed in for 8 minutes. 40 g of ethylene glycol monobutyl acetate was poured into the mixture and mixed for 20 minutes.

Specific Example 5

10 g of nitrocellulose and 40 g of distilled water were mixed for 5 minutes. 5 g of $NH_4OH$ (28%) and 40 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

Specific Example 6

10 g of nitrocellulose and 16.44 g of distilled water were mixed for 5 minutes. 5 g of $NH_4OH$ (28%) and 24.52 g of distilled water were combined, poured into the mixture and mixed for 5 minutes. 0.5 g of CMC-7H-1% was added and mixed for 8 minutes. 30 g of ethylene glycol monobutyl ether was poured into the mixture and mixed for 20 minutes.

The following are examples of the preferred method of preparing aqueous nitrocellulose:

Specific Example 7

10 g of nitrocellulose and 30 g of distilled water were mixed for 5 minutes. 5 g of $NH_4OH$ (28%) and 45 g of distilled water were combined and poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

Specific Example 8

10 g of nitrocellulose and 30 g of distilled water were mixed for 5 minutes. 5 g of $NH_4OH$ (28%) and 45 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

Specific Example 9

10 g of nitrocellulose and 16.44 g of distilled water were mixed for 5 minutes. 5 g of $NH_4OH$ (28%) and 24.52 g of distilled water were combined, poured into the mixture and mixed for 5 minutes. 0.5 g of CMC-7H-1% was added and mixed for 8 minutes. 46 g of ethylene glycol monobutyl ether was poured into the mixture and mixed for 30 minutes.

Specific Example 10

10 g of nitrocellulose and 16.44 g of distilled water were mixed for 5 minutes. 5 g of $NH_4OH$ (28%) and 24.52 g of distilled water were combined, poured into the mixture and mixed for 5 minutes. 0.5 g of CMC-7H-1% was added and mixed for 8 minutes. 46 g of ethylene glycol monobutyl ether was poured into the mixture and mixed for 20 minutes.

Specific Example 11

10 g of nitrocellulose and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

Specific Example 12

10 g of nitrocellulose and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl ether was poured into the mixture and mixed for 20 minutes.

The following are additional examples of the method of preparing aqueous nitrocellulose:

Specific Example 13

10 g of nitrocellulose and 30 g of distilled water were mixed for 5 minutes. 5 g of NH$_4$OH (28%) and 45 g of distilled water were combined, poured into the mixture and mixed for 5 minutes. 0.5 g of CMC-7H 1% was added and mixed for 8 minutes. 2 g of Zn(NH$_3$)3x(CO$_3$)x(Zinc Ammonia Carbonate Complex) and 8 g of distilled water were mixed in for 10 minutes. 35 g of ethylene glycol monobutyl acetate was poured into the mixture and mixed for 40 minutes.

Specific Example 14

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 20 g of ethylene glycol monobutyl ether and 26 g of isopropyl acetate were combined, poured into the mixture and mixed for 20 minutes.

Specific Example 15

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 30 g of ethylene glycol monobutyl ether and 16 g of diethylene glycol monoethyl ether were combined, poured into the mixture and mixed for 20 minutes.

Specific Example 16

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 30 g of ethylene glycol monobutyl ether and 16 g of ethylene glycol monobutyl acetate were combined, poured into the mixture and mixed for 25 minutes.

Specific Example 17

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 23 g of ethylene glycol monobutyl ether and 23 g of ethylene glycol monobutyl acetate were combined, poured into the mixture and mixed for 25 minutes.

Specific Example 18

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 30 g of ethylene glycol monobutyl ether and 16 g of ethylene glycol monobutyl acetate was combined, poured into the mixture and mixed for 25 minutes.

Specific Example 19

10 g of nitrocellulose and 20 g of distilled water were mixed for 5 minutes. 20 g of distilled water was poured into the mixture and mixed for 5 minutes. 0.5 g of CMC-7H-1% was added and mixed for 8 minutes. 40 g of N-methyl-2-pyrrolidone was poured into the mixture and mixed for 20 minutes.

Specific Example 20

10 g of nitrocellulose and 20 g of distilled water were mixed for 5 minutes. 20 g of distilled water was poured into the mixture and mixed for 5 minutes. 0.5 g of CMC-7H-1% was added and mixed for 8 minutes. 1 g of CO 630 was added. 40 g of ethylene glycol monobutyl acetate was poured into the mixture and mixed for 20 minutes.

II. Nitrocellulose Based Coatings

The nitrocellulose-based coatings of the present invention are obtained by mixing a proportional amount of acrylic-based polymers and aqueous nitrocellulose. Examples of polymers used in the present invention include but are not limited to A 1054, A 5050, BT 44, KRS 2411, Zinpol 259, Carboset 525, Carboset 526, R960 and KPS 5545. The preferred acrylic-based polymers are A 622, A 655 and A 1054. The invention can also include surfactants such as FC129 Fluorad, Surfynol DF-75, Surfynol S-104E, L 7001, A-196 and others known in the art. Specific silanes such as Z 6040, A 1100, 25-additive and Z-6020 as well as those known in the art may also be employed. The invention can also include titanates such as Tysor LA and Tysor LE. (Silanes and titanates are hydrolyzed 24 hours prior to usage to prevent concentrated areas in solution.) Colloidal silicas such as N 2326 and N 1115 and dispersants such as CT 136 and L 7602 may also be employed. Defoamers such as S-104E (also used as a wetting agent) may also be employed. Germicides such as Dowicide, parabens, ammonium hydroxide and others known in the art may also be added. A preferred germicide is Suttocide A, sold by Sutton Laboratory Inc, a GAF Company (aka ISP Manufacturing). Thickeners such as SCT 270, SCT 275, C525, CMC-7H and others known in the art may be added. A preferred thickener is Keltrol T, sold by Kelco Company, a division of Merck. The amount of germicides and thickeners added to the solution is based on the percentage level of solids in the solution. The amount of thickener used is in the range of about 0.4 to about 1.5% by weight and the amount of germicide used is also in the range of about 0.4 to about 1.5% weight. Solvents may be added to retard film formation and to allow better flow and freeze-thaw properties of the coating. Preferred solvents include ethanol (95%) or propylene glycol in the range of from about 8% by weight to about 10% by weight. Ultraviolet (UV) absorbers may also be employed to retard degradation of the coatings caused by UV radiation. Examples of suitable UV absorbers include Spectrasorb UV 5411 and UV 531 sold by American Cyanamid, Uvinol MS40 and Bs49 sold by BASF, Parsol MZX and 1789 sold by Givaudan and Tinuvin P sold by Ciba-Geigy. The amount of UV absorber used is in the range of about 0.2 to about 2% by weight.

The following methods were employed to formulate the nitrocellulose-based coatings. Generally, the material was placed in a 1000 ml beaker and a standard laboratory mixer was employed using a standard propeller, at room temperature. The mixer speed was set at 8.5 or at a speed great enough to form a vortex in the mixture. The solution was poured in a steady stream. A further step of decanting may be employed if necessary. Further illustrations of the basic method are depicted in the following examples.

Specific Example 22

20 g of Carboset 525 (15%) and 10 g of distilled water were mixed together in a vessel and added to 2.9 g (based on solid content) of aqueous nitrocellulose (prepared as described above) and mixed for 10 minutes. 20 g of Zinpol 529 was added and mixed for 10 minutes with the mixer speed increased to 8 setting. 10 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of distilled water and 10 g of ammonia hydroxide (10%) were poured together, mixed in a vessel, added to the above mixture and mixed for 10 minutes. 15 g of BT 44 was added and mixed for 10 minutes. 2.52 g of DF-75 (10%) at 0.5% level of solids was added and mixed for 15 minutes. 5.04 g of S-104E (1%) at 0.05% level of solids was added and mixed for 30 minutes. 5.04 g of FC-129 (0.01%) at 0.05% level of solids was added and mixed for 15 minutes. 2.52 g of Z 6040 (10%) at 0.5% level of solids was added and mixed for 15 minutes. 5.04 g of Tysor LA (10%) at 1% level of solids was added and mixed for 15 minutes. 2.52 g of Z 6020 (10%) at 0.5% level of solids was added and mixed for 15 minutes. 2.52 g of A 1100 (10%) at 0.5% level of solids was added and mixed for 15 minutes. 5 g of ethylene glycol at 10% of solids was added and mixed for 15 minutes. 2.52 g of L 7001 (1%) at 0.5% level of solids was added and mixed for 15 minutes. 0.3 g of N 2326 (10%) at 0.5% level of solids was added and mixed for 15 minutes. 0.3 g of N 1115 (10%) at 0.5% level of solids was added and mixed for 15 minutes. 2.52 g of A 196 (1%) at 0.5% level of solids was added and mixed for 15 minutes. 0.5 g of CMC-7H (1%) at 0.0625% level of solids was added and mixed for 30 minutes.

Specific Example 23

16 g of C 525 and 10 g of distilled water were combined. 2.9 g solid weight (based on solid content) of aqueous nitrocellulose (prepared as described above) was added. 10 g of BT 44 was added and mixed for 10 minutes. 25 g of A 622 was added and mixed for 10 minutes. 15 g of A 655 was added and mixed for 10 minutes. 15 g of Z 269 was added and mixed for 10 minutes. 5 g of KRS 2411 was added and mixed for 10 minutes. 20 g of A 1054 was added and mixed for 10 minutes. 10 g of distilled water was added and mixed for 10 minutes. 10 g of NH$_4$OH (10%) was added and mixed for 10 minutes. 2.2 g of DF 75 (10%) at 0.5% level of solids was added and mixed for 15 minutes. 4.4 g of S 104E (1%) at 0.05% level of solids was added and mixed for 30 minutes. 4.4 g of FC 129 (0.01%) at 0.05% level of solids was added and mixed for 30 minutes. 2.2 g of Z 6040 (10%) at 0.5% level of solids was added and mixed for 15 minutes. 4.4 g of Tysor LA (10%) at 1% level of solids was added and mixed for 15 minutes. 2.2 g of Z 6020 (10%) at 0.5% level of solids was added and mixed for 15 minutes. 2.2 g of A 1100 (10%) at 0.5% level of solids was added and mixed for 15 minutes. 5 g of ethylene glycol at 10% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.2 g of A 196 (1%0 at 0.5% level of solids was added and mixed for 15 minutes. 0.5 g of CMC-7H (1%) at 0.0625% level of solids was added and mixed for 30 minutes.

Specific Example 24

16 g of C 525 (15%) and 10 g of distilled water were combined. 2.9 g (based on solid content) of aqueous nitrocellulose (prepared as described above) was added. 20 g of Z 259 was added and mixed for 10 minutes. 10 g of KRS 2411 was added and mixed for 10 minutes. 25 g of A 622 and 15 g of A 655 was added and mixed for 10 minutes. 20 g of A 1054 was added and mixed for 10 minutes. 10 g of distilled water was added and mixed for 10 minutes. 10 g of NH$_4$OH (10%) was added and mixed for 10 minutes. 15 g of BT 44 was added and mixed for 10 minutes. 15 g of A 5050 was added and mixed for 10 minutes. 2.8 g of DF 75 (10%) at 0.5% level of solids was added and mixed for 15 minutes. 5.6 g of S 104E (1%) at 0.05% level of solids was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of Tysor LA (10%) at 1% level of solids was added and mixed for 15 minutes. 2.8 g of Z 6020 (10%) at 0.5% level of solids was added and mixed for 15 minutes. 2.8 g of A 1100 (10%) at 0.5% level of solids was added and mixed for 15 minutes. 2.8 g of L 7001 (1%) at 0.5% level of solids was added and mixed for 15 minutes. 5 g of ethylene glycol 10% of solids was added and mixed for 15 minutes. 1 g of 25-additive (3%) at 0.05% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

Specific Example 25

15 g of BT 44 and 25 g of A 622 were mixed together for 10 minutes. 10 g of A 1054 was added and mixed for 10 minutes. 15 g of A 655 was added and mixed for 10 minutes. 10 g of KRS 2411 was added and mixed for 10 minutes. 15 g of C 525 and 10 g of distilled water were combined, added to the above mixture and mixed for 10 minutes. 20 g of Z 259 was added and mixed for 10 minutes. 10 g of distilled water was added and mixed for 10 minutes. 10 g of NH$_4$OH (10%) was added and mixed for 10 minutes. 2.9 g (based on solid content) of aqueous nitrocellulose (prepared as described above) was added and mixed for 10 minutes. 4.72 g of S 104E (1%) at 0.05% level of solids was added and mixed for 30 minutes. 2.56 g of DF 75 (10%) at 0.5% level of solids was added and mixed for 15 minutes. 4.72 g of FC 129 (0.01%) at 0.5% level of solids was added and mixed for 30 minutes. 2.36 g of Z 6040 (10%) at 0.5% level of solids was added and mixed for 15 minutes. 4.72 g of Tysor LA (10%) at 1% level of solids was added and mixed for 15 minutes. 2.36 g of Z 6020 (10%) at 0.5% level of solids was added and mixed for 15 minutes. 2.36 g of A 1100 (10%) at 0.5% level of solids was added and mixed for 15 minutes. 2.36 g of L 7001 (1%) at 0.5% level of solids was added and mixed for 15 minutes. 4.6 g of ethylene glycol at 10% of solids was added and mixed for 15 minutes. 1.02 g of 25-additive at 0.05% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.36 g of A 196 (1%) at 0.5% level of solids was added and

Specific Example 26

2.9 g (based on solid content) of aqueous nitrocellulose (prepared as described above) was added to the vessel. 16 g of C 525 and 10 g of distilled water were combined, added to the vessel and mixed for 10 minutes. 25 g of A 622 was added and mixed for 10 minutes. 15 g of A 655 was added and mixed for 10 minutes. 15 g of Z 259 was added and mixed for 10 minutes. 15 g of BT 44 was added and mixed for 10 minutes. 20 g of A 1054 was added and mixed for 10 minutes. 10 g of NH$_4$OH (10%) was added and mixed for 10 minutes. 10 g of distilled water was added and mixed for 10 minutes. 2.25 g of DF 75 (10%) at 0.5% level of solids was added and mixed for 15 minutes. 4.5 g of S 104 E (1%) at 0.05% level of solids was added and mixed for 30 minutes. 4.5 g of FC 129 (0.01%) at 0.05% level of solids was added and mixed for 30 minutes. 2.25 g of Z 6040 (10%) at 0.5% level of solids was added and mixed for 15 minutes. 4.5 g of Tysor LA (10%) at 1% level of solids was added and mixed for 15 minutes. 2.25 g of Z 6020 (10%) at 0.5% level of solids was added and mixed for 15 minutes. 2.25 g of A 1100 (10%) at 0.5% level of solids was added and mixed for 15 minutes. 2.25 g of L 7001 (1%) at 0.5% level of solids was added and mixed for 15 minutes. 5 g of ethylene glycol at 10% of solids was added and mixed for 15 minutes. 1 g of 25-additive at 0.05% of solids was added and mixed for 15 minutes. 0.5 g of N 2325 (10%) at 0.5% level of solids was added and mixed for 15 minutes. 0.5 g of N 1115 (10%) at 0.5% level of solids was added and mixed for 15 minutes. 2.25 g of A 190 (1%) at 0.5% level of solids was added and mixed for 15 minutes. 0.5 g of CMC-7H-1% at 0.0625% level of solids was added and mixed for 30 minutes.

Specific Example 27

20 g of A 1054 was added to the vessel. 20 g of C 525 and 10 g of distilled water were combined, added to the vessel and mixed for 10 minutes. 15 g of A 655 was added and mixed for 10 minutes. 15 g of BT 44 was added and mixed for 10 minutes. 2.9 g (based on solid content) of aqueous nitrocellulose (prepared as described above) was added and mixed for 10 minutes. 25 g of A 622 was added and mixed for 10 minutes. 10 g of KRS 2411 was added and mixed for 10 minutes. 20 g of Z 259 was added and mixed for 10 minutes. 10 g of KRS 5545 was added and mixed for 10 minutes. 10 g of distilled water was added and mixed for 10 minutes. 10 g of NH$_4$OH (10%) was added and mixed for 10 minutes. 2.71 g of DF 75 (10%) at 0.5% level of solids was added and mixed for 15 minutes. 5.42 g of S 104 E (1%) at 0.05% level of solids was added and mixed for 30 minutes. 5.42 g of FC 129 (0.01%) at 0.05% level of solids was added and mixed for 30 minutes. 2.71 g of Z 6040 (10%) at 0.5% level of solids was added and mixed for 15 minutes. 5.42 g of Tysor LA (10%) at 1% level of solids was added and mixed for 15 minutes. 2.71 g of Z 6020 (10%) at 0.5% level of solids was added and mixed for 15 minutes. 2.71 g of A 1100 (10%) at 0.5% level of solids was added and mixed for 15 minutes. 2.71 g of L7001 (1%) at 0.5% level of solids was added and mixed for 15 minutes. 4.86 g of ethylene glycol at 8% of solids was added and mixed for 15 minutes. 1.25 g of 25-additive at 0.05% of solids was added and mixed for 15 minutes. 0.54 g of N 2325 (10%) at 0.5% volume of solids was added and mixed for 15 minutes. 0.54 g of N 1115 (10%) at 0.5% volume of solids was added and mixed for 15 minutes. 2.71 g of A 196 (1%) at 0.5% level of solids was added and mixed for 15 minutes. 0.54 g of CMC-7H-1% at 0.0625% level of solids was added and mixed for 30 minutes.

Specific Example 28

20 g of A 1054 and 15 g of BT 44 were combined and mixed for 10 minutes. 10 g of distilled water was added and mixed for 10 minutes. 15 g of A 655 was added and mixed for 10 minutes. 25 g of A 622 was added and mixed for 10 minutes. 2.9 g (based on solid content) of aqueous nitrocellulose (prepared as described above) was added and mixed for 10 minutes. 10 g of distilled water was added and mixed for 10 minutes. 10 g of NH$_4$OH (10%) was added and mixed for 10 minutes. 20 g of Z 259 was added and mixed for 10 minutes. 10 g of KRS 2411 was added and mixed for 10 minutes. 10 g of KRS 5545 was added and mixed for 10 minutes. 20 g of C 525 was added and mixed for 10 minutes. 2.71 g of DF 75 (10%) at 0.5% level of solids was added and mixed for 15 minutes. 5.42 g of S 104E (1%) at 0.05% level of solids was added and mixed for 30 minutes. 5.42 g of FC 129 (0.01%) at 0.05% level of solids was added and mixed for 30 minutes. 2.71 g of Z 6040 (10%) at 0.5% level of solids was added and mixed for 15 minutes. 5.42 g of Tysor LA (10%) at 1% level of solids was added and mixed for 15 minutes. 2.71 g of Z 6020 (10%) at 0.5% level of solids was added and mixed for 15 minutes. 2.71 g of A 1100 (10%) at 0.5% level of solids was added and mixed for 15 minutes. 2.71 g of L 7001 (1%) at 0.5% level of solids was added and mixed for 15 minutes. 4.86 g of ethylene glycol at 8% of solids was added and mixed for 15 minutes. 1.25 g of 25-additive at 0.05% of solids was added and mixed for 15 minutes. 0.54 g of N 2326 (10%) at 0.5% level of solids was added and mixed for 15 minutes. 0.54 g of N 1115 (10%) at 0.5% level of solids was added and mixed for 15 minutes. 2.71 g of A 196 (1%) at 0.5% level of solids was added and mixed for 10 minutes. 0.54 g of CMC-7H-1% at 0.0625% level of solids was added and mixed for 30 minutes.

Specific Example 29

2.9 g (based on solid content) of aqueous nitrocellulose (prepared as described above) was added to the vessel. 16 g of C 525 and 10 g of distilled water were combined, added to the vessel and mixed for 10 minutes. 10 g of BT 44 was added and mixed for 10 minutes. 25 g of A 622 was added and mixed for 10 minutes. 15 g of A 655 was added and mixed for 10 minutes. 15 g of Z 269 was added and mixed for 10 minutes. 20 g of A 1054 was added and mixed for 10 minutes. 10 g of distilled water was added and mixed for 10 minutes. 10 g of NH$_4$OH (10%) was added and mixed for 10 minutes. 2.2 g of DF 75 (10%) at 0.5% level of solids was added and mixed for 15 minutes. 4.4 g of FC 129 (0.01%) at. 0.05% level of solids was added and mixed for 30 minutes. 2.2 g of Z 6040 (10%) at 0.5% level of solids was added and mixed for 15 minutes. 4.4 g of Tysor LA (10%) at 1% level of solids was added and mixed for 15 minutes. 2.2 g of Z 6020 (10%) at 0.5% level of solids was added and mixed for 15 minutes. 2.2 g of A 1100 (10%) at 0.5% level of solids was added and mixed for 15 minutes. 5 g of ethylene glycol at 10% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 4.4 g of S 104E (1%) at 0.05% level of solids was added and mixed for 30 minutes.

Specific Example 30

2.9 g (based on solid content) of aqueous nitrocellulose (prepared as described above) and 15 g of BT 44 were combined and mixed for 10 minutes. 10 g of distilled water was added and mixed for 10 minutes. 20 g of A 1054 was added and mixed for 10 minutes. 15 g of A 655 was added and mixed for 10 minutes. 10 g of KRS 2411 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 20 g of Z 259 was added and mixed for 10 minutes. 25 g of A 622 was added and mixed for 10 minutes. 2.8 g of DF 75 (10%) at 0.5% level of solids was added and mixed for 15 minutes. 5.6 g of S 104E (1%) at 0.05% level of solids was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of Tysor LA (10%) at 1% level of solids was added and mixed for 15 minutes. 2.8 g of Z 6020 (10%) at 0.5% level of solids was added and mixed for 15 minutes. 2.8 g of A 1100 (10%) at 0.5% level of solids was added and mixed for 15 minutes. 2.8 g of L 7001 (1%) at 0.5% level of solids was added and mixed for 15 minutes. 5 g of ethylene glycol at 10% of solids was added and mixed for 15 minutes. 1 g of 25-additive (3%) at 0.05% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

Specific Example 31

20 g of A 1054 was added to the vessel. 20 g of C 525 and 10 g of distilled water were combined, added to the vessel and mixed for 10 minutes. 15 g of A 655 was added and mixed for 10 minutes. 15 g of BT 44 was added and mixed for 10 minutes. 2.9 g solid weight (based on solid content) aqueous nitrocellulose (prepared as described above) was added and mixed for 10 minutes. 25 g of A 622 was added and mixed for 10 minutes. 10 g of KRS 2411 was added and mixed for 10 minutes. 20 g of Z 259 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 2.71 g of DF 75 (10%) at 0.5% level of solids was added and mixed for 15 minutes. 5.42 g of S 104E (1%) at 0.05% level of solids was added and mixed for 30 minutes. 5.42 g of FC 129 (.01%) at 0.05% level of solids was added and mixed for 30 minutes. 2.71 g of Z 6040 (10%) at 0.5% level of solids was added and mixed for 15 minutes. 5.42 g of Tysor LA (10%) at 1% level of solids was added and mixed for 15 minutes. 2.71 g of Z 6020 (10%) at 0.5% level of solids was added and mixed for 15 minutes. 2.71 g of A 1100 (10%) at 0.5% level of solids was added and mixed for 15 minutes. 2.71 g of L 7001 (1%) at 0.5% level of solids was added and mixed for 15 minutes. 4.86 g of ethylene glycol at 8% of solids was added and mixed for 15 minutes. 1.25 g of 25-additive at 0.05% of solids was added and mixed for 15 minutes. 0.54 g of N 2326 (10%) at 0.5% level of solids was added and mixed for 15 minutes. 0.54 g of N 1115 (10%) at 0.5% level of solids was added and mixed for 15 minutes. 2.71 g of A 196 (1%) at 0.5% level of solids was added and mixed for 15 minutes. 0.54 g of CMC-7H (1%) at 0.0625% level of solids was added and mixed for 30 minutes.

Specific Example 32

20 g of A 1054 was added to the vessel. 20 g of C 525 and 10 g of distilled water were combined, added to the vessel and mixed for 10 minutes. 15 g of A 655 was added and mixed for 10 minutes. 15 g of BT 44 was added and mixed for 10 minutes. 2.9 g (based on solid content) of aqueous nitrocellulose (prepared as described above) was added and mixed for 10 minutes. 25 g of A 622 was added and mixed for 10 minutes. 10 g of KRS 2411 was added and mixed for 10 minutes. 20 g of Z 259 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 2.8 g of DF 75 (10%) at 0.5% level of solids was added and mixed for 15 minutes. 5.6 g of S 104E (1%) at 0.05% level of solids was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of Tysor LA (10%) at 1% level of solids was added and mixed for 15 minutes. 2.8 g of Z 6020 (10%) at 0.5% level of solids was added and mixed for 15 minutes. 2.8 g of 1100 (10%) at 0.5% level of solids was added and mixed for 15 minutes. 2.8 g of L 7001 (1%) at 0.5% level of solids was added and mixed for 15 minutes. 5 g of ethylene glycol at 10% of solids was added and mixed for 15 minutes. 1 g of 25-additive (3%) at 0.05% of solids was added and mixed for 15 minutes. 0.5 g of N 2326 (10%) at −0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

Specific Example 33

2.9 g (based on solid content) of aqueous nitrocellulose (prepared as described above) was added to the vessel. 16 g of C 525 (15%) and 10 g of distilled water were combined, added to the vessel and mixed for 10 minutes. 20 g of Z 259 was added and mixed for 10 minutes. 25 g of A 622 was added and mixed for 10 minutes. 15 g of A 655 was added and mixed for 10 minutes. 15 g of BT 44 was added and mixed for 10 minutes. 20 g of A 1054 was added and mixed for 10 minutes. 10 g of KRS 2411 was added and mixed for 10 minutes. 10 g of $NH_4OH$ (10%) was added and mixed for 10 minutes. 2.8 g of DF 75 (10%) at 0.5% level of solids was added and mixed for 15 minutes. 5.6 g of S 104E (1%) at 0.05% was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of Tysor LA (10%) at 1% level of solids was added and mixed for 15 minutes. 2.8 g of Z 6020 (10%) at 0.5% level of solids was added and mixed for 15 minutes. 2.8 g of A 1100 (10%) at 0.5% level of solids was added and mixed for 15 minutes. 2.8 g of L 7001 (1%) at (0.5%) level of solids was added and mixed for 15 minutes. 5 g of ethylene glycol at 10% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

Specific Example 34

2.9 g (based on solid content) of aqueous nitrocellulose (prepared as described above) was added to the vessel. 20 g of C 525 (15%) and 10 g of distilled water were combined, added to the vessel and mixed for 10 minutes. 20 g of Z 259 was added and mixed for 10 minutes. 25 g of A 622 was added and mixed for 10 minutes. 15 g of A 655 was added and mixed for 10 minutes. 15 g of BT 44 was added and mixed for 10 minutes. 20 g of A 1054 was added and mixed for 10 minutes. 10 g of KRS 2411 was added and mixed for 10 minutes. 10 g of NH$_4$OH (10%) was added and mixed for 10 minutes. 3 g of DF 75 (10%) at 0.6% level of solids was added and mixed for 15 minutes. 5.02 g of S 104E (1%) at 0.05% level of solids was added and mixed for 30 minutes. 5.02 g of FC 129 (0.01%) at 0.05% level of solids was added and mixed for 30 minutes. 5.01 g of Z 6040 (10%) at 1.02% level of solids was added and mixed for 15 minutes. 10 g of Tysor LA (10%) at 2% level of solids was added and mixed for 15 minutes. 5.01 g of Z 6020 (10%) at 1.02% level of solids was added and mixed for 15 minutes. 5.01 g of A 1100 (10%) at 1.02% level of solids was added and mixed for 15 minutes. 2.5 g of L 7001 (1%) at 0.5% level of solids was added and mixed for 15 minutes. 5 g of ethylene glycol at 10% of solids was added and mixed for 15 minutes. 0.25 g of N 2326 (10%) at 0.5% level of solids was added and mixed for 15 minutes. 0.25 g of N 1115 (10%) at 0.5% level of solids was added and mixed for 15 minutes. 2.5 g of A 196 (1%) at 0.5% level of solids was added and mixed for 30 minutes.

Specific Example 35

2.9 g (based on solid content) of aqueous nitrocellulose (prepared as described above) was added to the vessel. 20 g of C 525 (15%) and 10 g of distilled water were combined, added to the vessel and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 10 g of NH$_4$OH (10%) was added and mixed for 10 minutes. 3 g of DS 75 (10%) at 0.6% level of solids was added and mixed for 15 minutes. 5.6 g of FC 129 (0.01%) at 0.06% level of solids was added and mixed for 30 minutes. 5.01 g of S 104E (1%) at 0.05% level of solids was added and mixed for 30 minutes. 4 g of Z 6040 (10%) at 0.8% level of solids was added and mixed for 15 minutes. 10 g of Tysor LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 0.5 g of CMC-7H (1%) at 0.0625% level of solids was added and mixed for 30 minutes.

Specific Example 36

2.9 g (based on solid content) of aqueous nitrocellulose (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of Tysor LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 30 minutes.

Specific Example 37

2.9 g (based on solid content) of aqueous nitrocellulose (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of Tysor LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 3.01 g of SCT 270 1% of solids was added and mixed for 30 minutes.

Specific Example 38

2.9 g (based on solid content) of aqueous nitrocellulose (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of Tysor LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 2.20 g of SCT 270 0.75% of solids was added and mixed for 30 minutes.

Specific Example 39

2.9 g (based on solid content) of aqueous nitrocellulose (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of Tysor LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 2.04 g of SCT 270 at 0.75% level of solids was added and mixed for 30 minutes.

Specific Example 40

2.9 g (based on solid content) of aqueous nitrocellulose (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of Tysor LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 2.73 g of SCT 270 at 1% level of solids was added and mixed for 30 minutes.

III. Modified Polymers in Nitrocellulose Based Coatings

In a preferred method, polymers were modified with aqueous nitrocellulose prior to formulating the coatings. The modification optimizes the amount of nitrocellulose in solution producing an increase in the percent of nitrocellulose in the coating. The modified method produces coatings with increased clarity, viscosity, flexibility and hardness. The same basic method for formulating the coatings, as described above, is employed with the exception of using the modified polymers.

The following method was employed to formulate the modified polymers. Generally, polymer and aqueous nitrocellulose are mixed in a 1000 ml beaker. A water bath with a temperature of between about 70° to about 95° C. may be employed to accelerate the reaction. The solution is then placed in a container and sits for a few days to several weeks to allow for reaction. A furter step of decanting may be employed if necessary. The ratio of aqueous nitrocellulose to polymer varies for particular polymers. The optimum ratio for the preferred polymers are as follows:

0.06599 g nitrocellulose per 1 g A622
0.04 g nitrocellulose per 1 g A655
0.039 g nitrocellulose per 1 g A1054
0.0213 g nitrocellulose per 1 g KRS2411
0.022 g nitrocellulose per 1 g Z259

0.05748 g nitrocellulose per 1 g C525
0.0678 g nitrocellulose per 1 g BT44
0.0201 g nitrocellulose per 1 g R960

As described above, the general method for formulating nitrocellulose based coatings is employed using modified polymers. Illustrations of this basic method using modified polymers in the most preferred embodiment of the present invention is depicted in the following examples.

The following are examples of the methods of making the most preferred modified coatings:

Specific Example 49

360 g of modified A622 and 216 g of modified A655 was mixed for 20 minutes. 8.154 g of L7602 4% at 0.15% level of solids was added and mixed for 25 minutes. 6.53 g of S-77 1% at 0.03% level of solids was added and mixed for 30 minutes. 0.75 g of N1115 100% at 0.05% level of solids at 15% active was added and mixed for 25 minutes. 120 g of modified A1054 was added and mixed for 25 minutes. 57.3 g of ethanol 200% proof and 14.32 g of distilled water were added and mixed for 25 minutes. 2.18 g of suttocide A 100% at 0.5% level of solids at 50% active was added and mixed for 25 minutes. Thickener was added in quantum sufficient, 0.2% to 0.8% of total solids. The amount of solvent, defoamer, germicide and thickener was based on 37.75% of solids.

Specific Example 50

180 g of modified A622 and 108 g of modified A655 were mixed together for 10 minutes. 60 g of modified A1054 was added and mixed for 10 minutes. 4.54 g of L7602 4% at 0.15% of solids was added and mixed for 15 minutes. 3.63 g of Silwet 77 1% at 0.03% of solids was added and mixed for 25 minutes. 4.03 g of N1115 10% at 0.05% of solids at 15% active was added and mixed for 15 minutes. The amount of solvent, defoamer, germicide and thickener was based on 37.75% of solids. U.V. absorber 1% level of 10% solution is 6.795 g of Spectrasorb UV 5411.

Specific Example 51

180 g of modified A622 and 108 g of modified A655 were mixed together for 10 minutes. 60 g of modified A1054 was added and mixed for 10 minutes. 60 g of modified R960 was added and mixed for 10 minutes. 4.54 g of L7602 4% at 0.15% of solids was added and mixed for 15 minutes. 3.63 g of Silwet 77 1% at 0.03% of solids was added and mixed for 25 minutes. 4.03 g of N1115 10% at 0.05% of solids at 15% active was added and mixed for 15 minutes. The amount of solvent, defoamer, germicide and thickener was based on 37.75% of solids. U.V. absorber 1% level of 10% solution is 6.795 g of Spectrasorb UV 5411.

Specific Example 52

360 g of modified A622 and 216 g of modified A655 was mixed for 20 minutes. 120 g of modified A1054 was added and mixed for 20 minutes. 4.76 g of L7602 10% at 0.18% level of solids was added and mixed for 25 minutes. 7.93 g of S77 1% at 0.03% level of solids was added and mixed for 30 minutes. 0.88 g of N1115 100% at 0.05% level of solids at 15% active was added and mixed for 25 minutes. 2.12 g of Z6040 100% at 0.8% level of solids was added and mixed for 25 minutes. 8.46 g of Tysor LA 100% at 1.6% level of solids at 50% active was added and mixed for 25 minutes. 21.16 g of propylene glycol 100% at 0.8% level of solids was added and mixed for 25 minutes. 2.64 g of suttocide A 100% at 0.5% level of solids at 50% active was added and mixed for 25 minutes. The amount of solvent, defoamer, germicide and thickener was based on 38% of solids.

The following are examples of methods of making the preferred modified coatings:

Specific Example 53

480 g of modified A622 and 288 g of modified A655 was mixed for 20 minutes. 160 g of modified A1054 was added and mixed for 20 minutes. 160 g of modified KRS2411 was added and mixed for 20 minutes. 16.04 g of S104E 10% at 0.0205% level of solids at 50% active was added and mixed for 30 minutes. 23.27 g of FC129 0.2% at 0.006% level of solids at 50% active was added and mixed for 30 minutes. 14.67 g of L7602 4% at 0.15% level of solids was added and mixed for 25 minutes. 2.51 g of Z6040 100% at 0.64% of solids was added and mixed for 25 minutes. 10.09 g of Tysor LA 100% at 1.29% level of solids at 50% active was added and mixed for 25 minutes. 3.03 g of L7001 10% at 0.058% level of solids at 75% active was added and mixed for 25 minutes. 4.49 g of A196 10% at 0.068% level of solids at 85% active was added and mixed for 25 minutes. 3.92 g of N115 100% at 0.15% level of solids at 15% active was added and mixed for 25 minutes. 97.44 g of ethanol 200 proof was added and mixed for 25 minutes. Suttocide A was added in quantum sufficient. Thickeners were added in quantum sufficient. The amount of solvent, defoamer, germicide and thickener was based on 35.94% of solids.

Specific Example 54

180 g of modified A622 and 108 g of modified A655 were mixed for 10 minutes. 60 g of modified A1054 was added and mixed for 10 minutes. 60 g of modified KRS2411 was added and mixed for 10 minutes. 5.78 g of L7602 4% at 0.15% of solids was added and mixed for 15 minutes. 4.62 g of Silwet 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

Specific Example 55

180 g of modified A622 and 108 g of modified A655 were mixed for 10 minutes. 60 g of modified A1054 was added and mixed for 10 minutes. 72 g of modified KRS 2411 was added and mixed for 10 minutes. 6.07 g of L7602 4% at 0.15% of solids was added and mixed for 15 minutes. 6.63 g of S-104 E 1% at 0.0205% of solids at 50% active was added and mixed for 25 minutes. 19.40 g of FC129 0.1% at 0.006% of solids at 50% active was added and mixed for 25 minutes. 4.62 g of Z6040 20% at 0.64% of solids was added and mixed for 15 minutes. 13.91 g of Tysor LA 30% at 1.29% of solids at 50% active was added and mixed for 15 minutes. 12.51 g of L7001 1% at 0.058% of solids at 75% active was added and mixed for 15 minutes. 15.42 g of N1115 10% at 0.143% of solids at 15% active was added and mixed for 15 minutes. 12.37 g of A196 1% at 0.065% level of solids at 85% active was added and mixed for 15 minutes. The amount of solvent, defoamer, germicide and thickener was based on 38.50% of solids.

Specific Example 56

180 g of modified A622 and 108 g of modified A655 were mixed for 10 minutes. 60 g of modified A1054 was added and mixed for 10 minutes. 72 g of modified KRS2411 was added and mixed for 10 minutes. 5.78 g of L7602 4% at 0.15% of solids was added and mixed for 15 minutes. 4.62 g of Silwet 77 1% at 0.03% of solids was added and mixed for 25 minutes. 5.18 g of Z6040 20% at 0.64% of solids was added and mixed for 15 minutes. 13.91 g of Tysor LA 30% at 1.29% of solids at 50% active was added and mixed for 15 minutes. 5.14 g of N1115 10% at 0.05% of solids at 15% active was added and mixed for 15 minutes. The amount of solvent, defoamer, germicide and thickener was based on 38.50% of solids.

Specific Example 57

360 g of modified A622 and 216 g of modified A655 were mixed for 20 minutes. 120 g of modified A1054 was added and mixed for 20 minutes. 60 g of modified KRS2411 was added and mixed for 20 minutes. 5.17 g of L7602 10% at 0.18% level of solids was added and mixed for 25 minutes. 8.62 g of S77 10% at 0.03% level of solids was added and mixed for 30 minutes. 0.96 g of N1115 100% at 0.05% level of solids at 15% active was added and mixed for 25 minutes. 2.3 g of Z6040 100% at 0.8% level of solids was added and mixed for 25 minutes. 9.19 g of Tysor LA 100% at 1.6% level of solids at 50% active was added and mixed for 25 minutes. 22.98 g of propylene glycol 0.8% level of solids was added and mixed for 25 minutes. 2.87 g of suttocide A 100% at 0.5% level of solids at 50% active was added and mixed for 25 minutes. The amount of solvent, defoamer, germicide and thickener was based on 38% of solids.

Specific Example 58

180 g of modified A622 and 108 g of modified A655 were mixed for 20 minutes. 60 g of modified A1054 was added and mixed for 20 minutes. 2.38 g of L7602 10% at 0.18% of solids was added and mixed for 25 minutes. 3.97 g of S77 1% at 0.03% level of solids was added and mixed for 30 minutes. 0.44 g of N1115 100% at 0.05% level of solids at 15% active was added and mixed for 25 minutes. 30 g of modified KRS2411 was added and mixed for 20 minutes. 10.58 g of propylene glycol 100% at 0.8% level of solids was added and mixed for 25 minutes. 1.32 g of suttocide A 100% at 0.5% level solids at 50% active was added and mixed for 25 minutes. The amount of solvent, defoamer, germicide and thickener was based on 38% of solids.

Specific Example 59

180 g of modified A622 and 108 g of modified A655 were mixed for 20 minutes. 60 g of modified A1054 was added and mixed for 20 minutes. 30 g of modified KRS2411 was added and mixed for 20 minutes. 2.59 g of L7602 10% at 0.18% level of solids was added and mixed for 25 minutes. 4.31 g of S77 1% at 0.03% level of solids was added and mixed for 30 minutes. 0.48 g of N1115 100% at 0.05% level of solids at 15% active was added and mixed for 25 minutes. 11.49 g of propylene glycol at 0.8% level of solids was added and mixed for 25 minutes. 1.44 g of suttocide A 100% at 0.5% level of solids at 50% active was added and mixed for 25 minutes. The amount of solvent, defoamer, germicide and thickener was based on 38% of solids.

Specific Example 60

180 g of modified A622 and 108 g of modified A655 were mixed for 20 minutes. 1.97 g of L7602 10% at 0.18% level of solids was added and mixed for 25 minutes. 3.28 g of S77 1% at 0.03% level of solids was added and mixed for 30 minutes. 0.36 g of N1115 100% at 0.05% level of solids at 15% active was added and mixed for 25 minutes. 20 g of modified A1054 was added and mixed for 20 minutes. 0.88 g of Z6040 100% at 0.8% level of solids was added and mixed for 25 minutes. 3.5 g of Tysor LA 100% at 1.6% level of solids at 50% active was added and mixed for 25 minutes. 8.76 g of propylene glycol 100% at 0.8% level of solids was added and mixed for 25 minutes. 1.09 g of suttocide A 100% at 0.5% level of solids at 50% active was added and mixed for 25 minutes. The amount of solvent, defoamer, germicide and thickener was based on 38% of solids.

Specific Example 61

180 g of modified A622 and 108 g of modified A655 were mixed for 20 minutes. 1.97 g of L7602 10% at 0.18% level of solids was added and mixed for 25 minutes. 3.28 g of S77 1% at 0.03% level of solids was added and mixed for 30 minutes. 0.36 g of N1115 100% at 0.05% level of solids at 15% active was added and mixed for 25 minutes. 60 g of modified A1054 was added and mixed for 20 minutes. 30 g of modified KRS2411 was added and mixed for 20 minutes. 0.88 g of Z6040 100% at 0.8% level of solids was added and mixed for 25 minutes. 3.5 g of Tysor LA 100% at 1.6% level of solids at 50% active was added and mixed for 25 minutes. 8.76 g of propylene glycol 8% level of solids was added and mixed for 25 minutes. 1.09 g of suttocide A 100% at 0.5% level of solids at 50% active was added and mixed for 25 minutes.

Specific Example 62

180 g of modified A622 and 108 g of modified A655 were mixed for 10 minutes. 4.54 g of L7602 4% at 0.15% of solids was added and mixed for 15 minutes. 3.63 g of Silwet 77 1% at 0.03% of solids was added and mixed for 25 minutes. 4.03 g of N1115 10% at 0.05% of solids at 15% active was added and mixed for 15 minutes. The amount of solvent, defoamer, germicide and thickener was based on 38% of solids.

Specific Example 63

180 g of modified A622 and 108 g of modified A655 were mixed for 10 minutes. 6.07 g of L7602 4% at 0.15% of solids was added and mixed for 15 minutes. 6.63 g of S104E 1% at 0.0205% of solids at 50% active was added and mixed for 25 minutes. 19.40 g of FC129 1% at 0.006% of solids at 50% active was added and mixed for 25 minutes. 4.62 g of Z6040 20% at 0.64% of solids was added and mixed for 15 minutes. 13.91 g of Tysor LA 30% at 1.29% of solids at 50% active was added and mixed for 15 minutes. 12.51 g of L7001 1% at 0.058% of solids at 75% active was added and mixed for 15 minutes. 15.42 g of N1115 10% at 0.143% of solids at 15% active was added and mixed for 15 minutes. 12.37 g of A196 1% at 0.065% of solids at 85% active was added and mixed for 15 minutes. The amount of solvent, defoamer, germicide and thickener was based on 38% of solids.

Specific Example 64

180 g of modified A622 and 108 g of modified A655 were mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 1% at 0.006% of solids at 50% active was added and mixed for 25 minutes. 8.35 g of Z6040 20% at 0.64% of solids was added and mixed for 15 minutes. 22.45 g of Tysor LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38% of solids.

The following are additional examples of the method of making the modified coatings:

Specific Example 65

180 g of modified A622 and 108 g of modified A655 were mixed for 10 minutes. 60 g of modified A1054 was added and mixed for 10 minutes. 60 g of modified Z259 was added and mixed for 10 minutes. 5.78 g of L7602 4% at 0.15% of solids was added and mixed for 15 minutes. 4.62 g of Silwet 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

Specific Example 66

180 g of modified A622 and 108 g of modified A655 were mixed for 10 minutes. 60 g of modified A1054 was added and mixed for 10 minutes. 60 g of modified C525 was added and mixed for 10 minutes. 5.78 g of L7602 4% at 0.15% of solids was added and mixed for 15 minutes. 4.62 g of Silwet 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

Specific Example 67

180 g of modified A622 and 108 g of modified A655 were mixed for 10 minutes. 60 g of modified A1054 was added and mixed for 10 minutes. 60 g of modified BT44 was added and mixed for 10 minutes. 5.78 g of L7602 4% at 0.15% of solids was added and mixed for 15 minutes. 4.62 g of Silwet 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

Specific Example 68

180 g of modified A622 and 108 g of modified A655 were mixed together for 10 minutes. 120 g of modified A1054 was added and mixed for 10 minutes. 90 g of modified KRS2411 was added and mixed for 10 minutes. 90 g of modified of BT44 was added and mixed for 10 minutes. 90 g of modified Z259 was added and mixed for 10 minutes. 90 g of modified C525 was added and mixed for 10 minutes. 16.06 g of DF75 10% at 0.5435% of solids was added and mixed for 15 minutes. 12.13 g of S-104E 1% at 0.0205% of solids at 50% active was added and mixed for 25 minutes. 35.48 g of FC129 0.1% at 0.006% of solids at 50% active was added and mixed for 25 minutes. 9.46 g of Z6040 20% at 0.64% of solids was added and mixed for 15 minutes. 25.43 g of Tysor LA30% at 1.29% of solids at 50% active was added and mixed for 15 minutes. 22.87 of L7001 1% at 0.058% of solids at 75% active was added and mixed for 15 minutes. 28.19 g of N1115 10% at 0.143% of solids at 15% active was added and mixed for 15 minutes. 22.61 g of A196 1% at 0.065% of solids at 85% active was added and mixed for 15 minutes. The amount of solvent, defoamer, germicide and thickener was based on 38.50% of solids.

Specific Example 69

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified BT44 was added and mixed for 10 minutes. 90 g of modified C525 was added and mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of Tysor LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

Specific Example 70

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of Tysor LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

Specific Example 71

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 9.79 g of L7602 4% at 0.15% of solids was added and mixed for 15 minutes. 7.83 g of Silwet 77 1% at 0.03% of solids was added and mixed for 25 minutes. 8.35 g of Z6040 20% at 0.64% of solids was added and mixed for 15 minutes. 22.45 g of Tysor LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

Specific Example 72

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 9.79 g of L7602 4% at 0.15% of solids was added and mixed for 15 minutes. 10.71 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of Tysor LA 30% at 1.29% of solids at 50% active was added and mixed for 15 minutes. 20.19 g of L7001 1% at 0.058% of solids at 75% active was added and mixed for 15 minutes. 26.11 g of N1115 10% at 0.15% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

Specific Example 73

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 9.79 g of L7602 4% at 15% of solids was added and mixed for 15 minutes. 7.83 g of Silwet 77 1% at 0.03% of solids was added and mixed for 25 minutes. 8.35 g of Z6040 20% at 0.64% of solids was added and mixed for 15 minutes. 22.45 g of Tysor LA 30% at 1.29% of solids at 50% active was added and mixed for 15 minutes. 26.03 g of N1115 10% at 0.15% of solids at 15% active was added and mixed for 15 minutes. The amount of solvent, defoamer, germicide and thickener was based on 38.50% of solids.

Specific Example 74

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of Tysor LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

IV. Pigmented Coatings

Pigmented coatings are obtained by adding dispersed treated pigments to the nitrocellulose-based coatings (both nitrocellulose-based coatings with modified polymers and nitrocellulose-based coatings with unmodified polymers). The dispersed treated pigments are obtained by repeatedly mixing the pigments with silanes, titanates and other additives, and heating until desiccation. Distilled water may be added at each step to allow for proper mixing. The treated pigments are then milled with a wetting agent and dispersing surfactant. The milled pigment is added to the appropriate coating formula.

Generally, the pigments are placed in a glass beaker and silane is added. Pigments employed in the present invention include but are not limited to D & C red 21, D & C yellow, D & C cosmetic iron blue, D & C T102 and D & C cosmetic dioxide. Silanes used in the present invention include but are not limited to Z 6040, 25-additive, A 1100, and Z 6020. After mixing the pigments and silane for about 5 minutes, the vessel is heated with occassional stirring until all the liquid is desiccated. Titanate is then added and the mass is mixed for about 5 minutes. The titanates employed in the present invention include Tysor TE, and Tysor LA. The mass is then heated with occassional stirring until all the liquid has dried. Again, silane is added and the mass is mixed for about 5 minutes. The mass is heated and stirred until desiccated. Silane is added and mixed for about 5 minutes. The mass is again heated and stirred until desiccated. The material is placed in a mill, then dispersed with a wetting agent for about 30 minutes. The preferred wetting agent of the present invention is S-104E but others known in the art may be employed. Finally, a dispersing surfactant is added and the material is placed in a mill for about 90 minutes. The preferred dispersing surfactants of the present invention are CT 136 and L7602. The dispersed treated pigments are then added to the coating prepared as described above and mixed for about 20 minutes.

The following examples employ the general technique described above to formulate the dispersed treated pigments:

Specific Example 75

0.55 g D&C red 6, 0.45 g D&C red 34 and 1 g Z6040 (10%) of solids were combined in a glass beaker, mixed for 5 minutes and microwaved at high for 5 minutes. 4 g Tysor TE (10%) at 26% of solids at 50% active was added, mixed for 5 minutes and microwaved for 5 minutes at high. 5 g of distilled water was added. 0.5 g of CMC-7H (1%) at 0.0625% level of solids was added and mixed for 5 minutes and microwaved for 5 minutes at high.

Specific Example 76

12 g D&C red 6 and 24 g Z 6040 (10%) at 20% of solids were combined in a glass beaker, mixed for 20 minutes and microwaved at high for 10 minutes. 24 g of Tysor TE (10%) at 10% of solids at 50% active was added. 60 g of distilled water was added. The combination was mixed for 5 minutes and microwaved at high for 10 minutes. 6 g of CMC-7H (1%) at 0.5% of solids was added and mixed for 5 minutes and microwaved for 5 minutes at high.

Specific Example 77

14 g of D&C red 6 and 14 g of Z 6040 (10%) at 10% of solids were combined in a glass beaker, mixed for 5 minutes and microwaved at high for 10 minutes. 28 g of Tysor LA (10%) at 10% of solids at 50% active was added. The combination was mixed for 5 minutes and microwaved at high for 10 minutes. 14 g of Z 6020 (10%) at 10% of solids was added, mixed for 5 minutes and microwaved at high for 10 minutes. 7 g of CMC-7H (1%) at 0.5% solids was mixed for 5 minutes and microwaved for 10 minutes at high.

Specific Example 78

14 g of D&C red 6 and 14 g of Z 6040 (10%) at 10% of solids were combined in a glass beaker, mixed for 5 minutes and microwaved at high for 10 minutes. 28 g of Tysor LA (10%) at 10% of solids at 50% active was added. The combination was mixed for 5 minutes and then microwaved at high for 10 minutes. 14 g of Z 6020 (10%) at 10% of solids was added, mixed for 5 minutes and microwaved at high for 10 minutes. 14 g of A 1100 (10%) at 10% of solids was added, mixed for 5 minutes and microwaved at high for 10 minutes. 7 g of CMC-7H (1%) at 0.5% solids was added, mixed for 5 minutes and microwaved for 10 minutes at high.

Specific Example 79

4.02 g of D&C red 7, 0.8 g of D&C red 6, 1.8 g of D&C $TiO_2$, 3.13 g of D&C red 34, 0.01 g of D&C cosmetic iron blue, 0.25 g of D&C yellow 5 and 0.02 g of D&C cosmetic dioxide (total of 10 g of pigment) and 10 g of Z 6040 (10%) at 10% of solids were combined in a glass beaker, mixed for 5 minutes and microwaved at high for 10 minutes. 30 g of Tysor LA (10%) at 15% of solids at 50% active was added. The combination was mixed for 5 minutes and microwaved at high for 10 minutes. 10 g of Z 6020 (10%) at 10% of solids was added, mixed for 5 minutes and microwaved at high for 10 minutes. 10 g of A 1100 (10%) at 10% of solids was added, mixed for 5 minutes and microwaved at high for 10 minutes. 5 g of CMC-7H (1%) at 0.5% of solids was added and mixed for 5 minutes and microwaved for 5 minutes at high. 6.67 g of NAlco 1115 100% at 10% of solids at 15% active and 10 g of distilled water were added, mixed for 5 minutes and microwaved at high for 5 minutes.

Specific Example 80

4.02 g of D&C red 7, 0.8 g of D&C red 6, 1.8 g of D&C $TiO_2$, 3.13 g of D&C red 34, 0.01 g of D&C cosmetic iron blue, 0.25 g of D&C yellow 5, 0.02 of D&C cosmetic dioxide (total of 10 g of pigment) and 10 g of Z 6040 (10%) at 10% of solids were combined in a glass beaker, mixed for 5 minutes and microwaved at high for 10 minutes. 30 g of Tysor LA (10%) at 15% of solids at 50% active was added. The combination was mixed for 5 minutes and microwaved at high for 10 minutes. 10 g of Z 6020 (10%) at 10% of solids was added, mixed for 5 minutes and microwaved at high for 10 minutes. 10 g of A 1100 (10%) at 10% of solids was added, mixed for 5 minutes and microwaved at high for 10 minutes. 50 g of CMC-7H (1%) at 5% of solids was added and mixed for 5 minutes and microwaved for 5 minutes at high.

Specific Example 81

4.02 g of D&C red 7, 0.08 of D&C red 6, 1.8 g of D&C $TiO_2$, 3.13 g of D&C red 34, 0.01 g of D&C cosmetic iron blue, 0.25 g of D&C yellow 5, 0.02 g of D&C cosmetic dioxide (total of 10 g of pigment) and 20 g of Z 6040 (10%) of 20% of solids were combined in a glass beaker, mixed for 10 minutes and microwaved at high for 5 minutes. 80 g of Tysor LA (10%) at 40% of solids at 50% active was added. The combination was mixed for 5 minutes and microwaved at high for 10 minutes. 20 g of Z 6020 (10%) at 20% of solids was added, mixed for 5 minutes and microwaved at high for 10 minutes. 20 g of A 1100 (10%) at 20% of solids was added, mixed for 5 minutes and microwaved at high for 10 minutes.

Specific Example 82

10 g of pigment, 5 g of Z6040 20% at 10% level of solids and 10 g of distilled water were combined in a glass beaker, mixed for 5 minutes and microwaved for 4 minutes at high. 20 g of Tysor LA or Tysor TE 30% at 30% of solids at 50% active, 1 g of 25-additive 100% at 10% of solids, 5 g of Z6020 20% at 10% level of solids and 10 g of distilled water were combined and added to the above mixture. The mixture was then mixed for 5 minutes and microwaved for 4 minutes at high. 5 g of A1100 20% at 10% level of solids and 10 g of distilled water were combined and added to the above mixture. The mixture was then mixed for 5 minutes and microwaved for 4 minutes at high. 30 g of CMC-7H 1% at 3% of solids was then mixed for 5 minutes and microwaved for 4 minutes at high. 20 g of Nalco 1115 100% at 30% of solids at 15% active and 10 g of distilled water were combined and added to the above mixture. The mixture was then mixed for 5 minutes and microwaved at high for 4 minutes.

Specific Example 83

10 g of pigment, 10 g of Z6040 20% at 20% level of solids and 10 g of distilled water were combined in a glass beaker, mixed for 5 minutes and microwaved for 4 minutes at high. 33.3 g of Tysor LA or Tysor TE 30% at 50% of solids at 50active, 2 g of 25-additive 100% at 20% of solids, 10 g of Z6020 20% at 20% level of solids and 10 g of distilled water were combined and added to the above mixture. The mixture was then mixed for 5 minutes and microwaved for 4 minutes at high. 10 g of A1100 20% at 20% level of solids and 10 g of distilled water were combined and added to the above mixture. The mixture was then mixed for 5 minutes and microwaved for 4 minutes at high. 40 g of CMC-7H 1% at 4% of solids was then mixed for 5 minutes and microwaved for 4 minutes at high. 26.67 g of Nalco 1115 100% at 40% of solids at 15% active and 10 g of distilled water were combined and added to the above mixture. The mixture was then mixed for 5 minutes and microwaved at high for 4 minutes.

Specific Example 84

10 g of pigment, 15 g of Z6040 20% at 30% level of solids and 10 g of distilled water were combined in a glass beaker, mixed for 5 minutes and microwaved for 4 minutes at high. 40 g of Tysor LA or Tysor TE 30% at 60% of solids at 50% active, 5 g of 25-additive 100% at 50% of solids, 20 g of Z6020 20% at 40% level of solids and 10 g of distilled water were combined and added to the above mixture. The mixture was then mixed for 5 minutes and microwaved for 4 minutes at high. 20 g of A1100 20% at 40% level of solids and 10 g of distilled water were combined and added to the above mixture. The mixture was then mixed for 5 minutes and microwaved for 4 minutes at high. 10 g of CMC-7H 1% at 1% of solids was then mixed for 5 minutes and microwaved for 4 minutes at high. 10 g of Nalco 1115 100% at 15% of solids at 15% active and 10 g of distilled water were combined and added to the above mixture. The mixture was then mixed for 5 minutes and microwaved at high for 4 minutes.

Specific Example 85

10 g of pigment, 20 g of Z6040 20% at 40% level of solids and 10 g of distilled water were combined in a glass beaker, mixed for 5 minutes and microwaved for 4 minutes at high. 46.67 g of Tysor LA or Tysor TE 30% at 70% of solids at 50% active, 6 g of 25-additive 100% at 60% of solids, 20 g of Z 6020 20% at 40% level of solids and 10 g of distilled water were combined and added to the above mixture. The mixture was then mixed for 5 minutes and microwaved for 4 minutes at high. 20 g of A1100 20% at 40% level of solids and 10 g of distilled water were combined and added to the above mixture. The mixture was then mixed for 5 minutes and microwaved for 4 minutes at high. 50 g of CMC-7H 1% at 5% of solids was then mixed for 5 minutes and microwaved for 4 minutes at high. 36.67 g of Nalco 1115 100% at 55% of solids at 15% active and 10 g of distilled water were combined and added to the above mixture. The mixture was then mixed for 5 minutes and microwaved at high for 4 minutes.

The following example employs the most preferred method of formulating the pigmented coatings:

Specific Example 86

The coating is prepared by the following method.

360 g of modified A622 and 216 g of modified A655 were mixed for 20 minutes. 120 g of modified A1054 was added and mixed for 25 minutes. 8.154 g of L7602 4% at 0.15% level of solids was added and mixed for 25 minutes. 6.53 g of S-77 1% at 0.03% level of solids was added and mixed for 30 minutes. 0.75 g of N1115 100% at 0.05% level of solids at 15% active was added and mixed for 25 minutes. 15.76 g of propylene glycol at 8% level were added and mixed for 25 minutes. 2.18 g of suttocide A 100% at 0.5% level of solids at 50% active was added and mixed for 25 minutes. Thickener was added in quantum sufficient, 0.2% to 0.8% of total solids. The amount of solvent, defoamer, germicide and thickener was based on 37.75% of solids.

The pigments are treated by the following technique.

6 g of Ba lake #6 red, 2 g of Orange #5 AL lake, 2 g of red #34 Ca lake and 10 g of red #7 Ca lake were combined (20 g of pigment). 20 g of Z6040 20% at 20% level of solids, 10 g of distilled water and the pigment were mixed for 5 minutes and microwaved for 6 minutes at high. 16.08 g of Tysor LA 100% at 40% level of solids at 50% active and 10 g of distilled water were added, mixed for 5 minutes and microwaved for 6 minutes at high. 20 g of Z6020 20% at 20% level of solids and 10 g of distilled water was added, mixed for 5 minutes and microwaved for 6 minutes at high. 20 g of A1100 20% at 20% level of solids and 10 g of distilled water was added, mixed for 5 minutes and microwaved for 6 minutes at high. 40.2 g of CMC7H 1% at 2% level of solids was added, mixed for 10 minutes and microwaved for 6 minutes at high. 40 g of N1115 100% at 30% level of solids at 15% active and 20 g of distilled water were added, mixed for 10 minutes and microwaved for 6 minutes at high. 8 g of the above treated pigments was added to a metal cylinder with metal balls. 8 g of 77 Silwet 1% at 1% level of solids was added and milled for 60 minutes. 1.44 g of L7602 100% at 18% level of solids was added and milled for 120 minutes.

The treated pigments from above are dispersed by the following technique.

8 g of treated pigment and 4 g of CMC7H 10% at 0.5% level of solids were mixed and milled for 15 minutes. 8 g of S104E 2% at 1% level of solids at 50% active was added and milled for 30 minutes. 1.44 g of L7602 100% at 18% level of solids was added and milled for 90 minutes. The coating from above was added in quantum sufficient for desired intensity of color.

The following example employs a preferred method of formulating the pigmented coatings:

Specific Example 87

The coating is prepared by the following method.

360 g of modified A622 and 216 g of modified A655 were mixed for 20 minutes. 120 g of modified A1054 was added and mixed for 25 minutes. 120 g of modified R960 was added and mixed for 25 minutes. 8.154 g of L7602 4% at 0.15% level of solids was added and mixed for 25 minutes. 6.53 g of S-77 1% at 0.03% level of solids was added and mixed for 30 minutes. 0.75 g of N1115 100% at 0.05% level of solids at 15% active was added and mixed for 25 minutes. 15.76 g of propylene glycol at 8% level were added and mixed for 25 minutes. 2.18 g of suttocide A 100% at 0.5% level of solids at 50% active was added and mixed for 25 minutes. Thickener was added in quantum sufficient, 0.2% to 0.8% of total solids. The amount of solvent, defoamer, germicide and thickener was based on 37.75% of solids.

The pigments are treated by the following technique.

6 g of Ba lake #6 red, 2 g of Orange #5 AL lake, 2 g of red #34 Ca lake and 10 g of red #7 Ca lake were combined (20 g of pigment). 20 g of Z6040 20% at 20% level of solids, 10 g of distilled water and the pigment were mixed for 5 minutes and microwaved for 6 minutes at high. 16.08 g of Tysor LA 100% at 40% level of solids at 50% active and 10 g of distilled water were added, mixed for 5 minutes and microwaved for 6 minutes at high. 20 g of Z6020 20% at 20% level of solids and 10 g of distilled water was added, mixed for 5 minutes and microwaved for 6 minutes at high. 20 g of A1100 20% at 20% level of solids and 10 g of distilled water was added, mixed for 5 minutes and microwaved for 6 minutes at high. 40.2 g of CMC7H 1% at 2% level of solids was added, mixed for 10 minutes and microwaved for 6 minutes at high. 40 g of N1115 100% at 30% level of solids at 15% active and 20 g of distilled water were added, mixed for 10 minutes and microwaved for 6 minutes at high. 8 g of the above treated pigments was added to a metal cylinder with metal balls. 8 g of 77 Silwet 1% at 1% level of solids was added and milled for 60 minutes. 1.44 g of L7602 100% at 18% level of solids was added and milled for 120 minutes.

The treated pigments from above are dispersed by the following technique.

8 g of treated pigment and 4 g of CMC7H 10% at 0.5% level of solids were mixed and milled for 15 minutes. 8 g of S104E 2% at 1% level of solids at 50% active was added and milled for 30 minutes. 1.44 g of L7602 100% at 18% level of solids was added and milled for 90 minutes. The coating from above was added in quantum sufficient for desired intensity of color.

The following example employs a preferred method of formulating the pigmented coatings:

Specific Example 88

The coating is prepared by the following method.

480 g of modified A622 and 288 g of modified A655 were mixed for 20 minutes. 160 g of modified A1054 was added and mixed for 20 minutes. 160 g of modified KRS2411 was added and mixed for 20 minutes. 16.04 g of S104E 10% at 0.0205% level of solids at 50% active was added and mixed for 30 minutes. 23.27 g of FC129 0.2% at 0.006% level of solids at 50% active was added and mixed for 30 minutes. 14.67 g of L7602 4% at 0.15% level of solids was added and mixed for 25 minutes. 2.51 g of Z6040 100% at 0.64% of solids was added and mixed for 25 minutes. 10.09 g of Tysor LA 100% at 1.29% level of solids at 50% active was added and mixed for 25 minutes. 3.03 g of L7001 10% at 0.058% level of solids at 75% active was added and mixed for 25 minutes. 4.49 g of A196 10% at 0.068% level of solids at 85% active was added and mixed for 25 minutes. 3.92 g of N115 100% at 0.15% level of solids at 15% active was added and mixed for 25 minutes. 97.44 g of ethanol 200 proof was added and mixed for 25 minutes. Suttocide A was added in quantum sufficient. Thickeners were added in quantum sufficient.

The pigments are treated by the following technique.

20 g of pigment, 20 g of Z6040 20% at 20% level of solids and 10 g of distilled water were mixed for 5 minutes and microwaved for 6 minutes at high. 40 g of Tysor LA 40% at 40% level of solids at 50% active was added, mixed for 5 minutes and microwaved for 6 minutes at high. 6 g of #25 (Dow Corning) at 100% at 30% level of solids, 20 g of Z6020 20% at 20% level of solids and 10 g of distilled water was added, mixed for 5 minutes and microwaved for 6 minutes at high. 20 g of A1100 20% at 20% level of solids and 10 g of distilled water was added, mixed for 5 minutes and microwaved for 6 minutes at high. 40 g of CMC7H 1% at 20% level of solids and 20 g of distilled water were added, mixed for 5 minutes and microwaved for 6 minutes at high. 40 g of N1115 100% at 30% level of solids at 15% active was added, mixed for 5 minutes and microwaved for 6 minutes at high.

The treated pigments from above are dispersed by the following technique.

5 g of treated pigment, 5 g of S77 1% at 1% level of solids, and 20 g of distilled water were placed in a shaker and were shaken for 60 minutes. 0.9 g of L7602 100% at 18% level of solids was added and shaken for 120 minutes. The treated and dispersed pigments were then added to 120 g of the above coating.

What is claimed is:

1. A method for preparing an aqueous nitrocellulose composition comprising the following steps:
    a) mixing water and nitrocellulose in a ratio of from about 2 parts by weight water per part by weight nitrocellulose to about 10 parts by weight water per part by weight nitrocellulose, thereby forming a water-nitrocellulose mixture;
    b) heating the water-nitrocellulose mixture to from about 70° C. to about boiling;
    c) adding a solvent to the water-nitrocellulose mixture in a ratio of from about 2 parts by weight solvent to about 10 parts by weight solvent per part by weight nitrocellulose present in the water-nitrocellulose mixture thereby forming a water-nitrocellulose solvent mixture;
    d) heating the water-nitrocellulose solvent mixture to from about 70° C. to about boiling; and
    e) mixing the water-nitrocellulose solvent mixture thereby forming an aqueous nitrocellulose composition.

2. The method of claim 1 wherein the step of mixing water and nitrocellulose further comprises mixing water and nitrocellulose in increments.

3. An aqueous nitrocellulose composition consisting essentially of nitrocellulose, water and solvent in a ratio of from about 0.5 to about 4 parts by weight water and from about 1 to about 7 parts by weight solvent, per part by weight nitrocellulose.

4. The method of claim 1 wherein the solvent is selected from the group consisting of propylene glycol monopropyl ether, ethylene glycol monopropyl ether, ethyl 3-ethoxypropionate, isopropyl alcohol with ethylene glycol monobutyl ether, dipropylene glycol monobutyl ether, dipropylene glycol methyl ether, ethyl alcohol, propylene glycol methyl acetate, isopropyl acetate, N-methyl-2-pyrrolidone, isopropyl alcohol, propylene glycol methyl ether, propylene glycol monobutyl ether, ethylene glycol monobutyl ether and diethylene glycol monoethyl ether.

5. The method of claim 1 wherein the aqueous nitrocellulose composition has a pH of from about 2 to about 6.

6. An aqueous nitrocellulose composition consisting essentially of nitrocellulose, water and solvent in a ratio of from about 2 to about 10 parts by weight water and from about 2 to about 10 parts by weight solvent, per part by weight nitrocellulose.

7. An aqueous nitrocellulose solution obtained by the method of claim 1.

8. An aqueous nitrocellulose solution comprising nitrocellulose, water and solvent in a ratio of from about 0.5 to about 4 parts by weight water and from about 1 to about 7 parts by weight solvent, per part by weight nitrocellulose.

* * * * *